United States Patent [19]

Pittz et al.

[11] Patent Number: 4,780,249

[45] Date of Patent: Oct. 25, 1988

[54] IRRITATION INHIBITING DETERGENT FORMULATIONS

[75] Inventors: Eugene P. Pittz, Lincoln, Nebr.; Richard V. Smerbeck, Hackettstown, N.J.

[73] Assignee: Warner-Lambert Company, Morris Plains, N.J.

[21] Appl. No.: 867,116

[22] Filed: May 23, 1986

Related U.S. Application Data

[62] Division of Ser. No. 684,819, Dec. 20, 1984, abandoned.

[51] Int. Cl.⁴ .......................... C11D 1/14; C11D 1/62
[52] U.S. Cl. .................................. 252/547; 252/550; 252/553; 252/558; 252/DIG. 14
[58] Field of Search .............. 252/550, 558, 553, 547, 252/545, DIG. 14

[56] References Cited

U.S. PATENT DOCUMENTS

| | | | |
|---|---|---|---|
| 3,998,948 | 12/1976 | Vanlerberghe et al. | 424/170 |
| 4,014,995 | 3/1977 | Juliano et al. | 424/168 |
| 4,087,518 | 5/1978 | Smith et al. | 424/70 |
| 4,412,944 | 11/1983 | Panzer et al. | 252/551 |

FOREIGN PATENT DOCUMENTS 10034846  9/1981  European Pat. Off. .

*Primary Examiner*—Prince E. Willis
*Attorney, Agent, or Firm*—Daniel A. Scola, Jr.; Howard Olevsky; Henry C. Jeanette

[57] ABSTRACT

A process and composition for inhibiting surfactant irritation and insult comprising an aqueous solution of a surfactant and an effective amount of an irritation inhibitor selected from the group consisting of lecithin, sodium cetearyl sulfate, an amino acid, cocamine compounds, amine oxides, glyceryl monoesters, ethoxylated monocarboxylic acids, ethoxylated hydroxyl compounds and mixtures thereof.

21 Claims, No Drawings

IRRITATION INHIBITING DETERGENT FORMULATIONS

This is a divisional of co-pending application Ser. No. 684,819 filed on Dec. 20, 1984, abandoned.

FIELD OF INVENTION

This invention relates to a personal care cleansing agent based on an aqueous solution of a detergent composition and a cosolvent irritation inhibitor.

BACKGROUND OF THE INVENTION

A major problem in developing cleansing products for skin and hair is the fact that those detergents which are the most efficient cleansing agents are most irritating to skin tissue. Hence, it is generally necessary to "trade off" cleansing efficiency with mildness to tissue.

There have been attempts to resolve this problem, but only weak compromises have been achieved. Agents, which complex with surfactants or compete with surfactants at potential binding sites or alter partition coefficients of surfactants generally interfere with the surface activity and, hence, the efficacy of the surfactant. Similarly, chemical modification of surfactants to impart mildness generally results in a loss of cleansing efficiency.

U.S. Pat. No. 4,420,410 discloses the combination of a betaine solution and a fatty acid monoglyceride. The monoglyceride acts as a thickener and is alleged to improve mucous membrance compatibility.

Japanese patent Early-Disclosure No. 83-125797 teaches the use of a moisture retaining agent for inhibiting the irritation to the skin caused by anionic surfactants. The moisture retaining agents taught are polyhydric alcohols such as glycerol, sorbitol and mannitol, monosaccharides such as glucose and mannose and oligosaccharides such as sucrose and maltose. The test used to determine irritation inhibition effectiveness is a closed human-body patch test. This test is not a severe test and the results are not necessarily indicative of the skin irritation hazard which might be encountered from prolonged exposure, e.g. cleansing cream as compared to shampoos which are rapidly and completely rinsed away. What is required is a compound to inhibit skin irritation caused by detergents which is effective under severe test conditions when used at low concentrations.

SUMMARY OF THE INVENTION

It has surprisingly been found that the glycerol monoesters, amine oxides, cocamide compounds, Na Cetearyl SO$_4$, lecithin, and certain aminoacids are effective skin irritation inhibitors for compositions using as a detergent, anionic, cationic or nonionic detergents. These inhibitors include alanine, glycine, lecithin, cocamide DEA, cocamide MEA, cocamide betaine, N-cocomorpholine oxide, oleamine oxide, lauramine oxide; glyceryl monolaurate, monooleate, monostearate and hydroxystearate, polyethylene glycol stearate; and hexylene glycol.

The irritation inhibitors of this invention are distinguished from the prior art in that they offer substantially improved protection at lower concentrations. Furthermore, no deactivation or reduction of degreasing capability of the detergent occurs.

DETAILED DESCRIPTION

This invention relates to a detergent composition comprising a detergent and an irritation inhibitor. The composition of this invention is a detergent composition which retains substantially all of the cleansing and degreasing characteristic of the detergent per se while being substantially nonirritating. The mildness characteristic of the detergent composition is achieved by combining the detergent with an irritation inhibitor. While the irritation inhibitors of this invention are useful with a wide range of detergents including nonionic and cationic detergents, they are most advantageously used in conjunction with anionic detergents, e.g. linear alkyl benzene sulfonates (LAS). The particular LAS which are preferred are sodium linear alkylbenzene-sulfonates.

The surfactants when used in water solutions are utilized at a concentration of at least 0.1 wt.% based on the weight of solution more preferably at least 0.25 wt.%. Generally the surfactant is utilized at a concentration of about 0.25 to about 10 wt.% based on the total weight of solution, preferably about 0.25 to about 5 wt.%.

The classes of compounds which are suitable for use as the irritation inhibitors of this invention include amino acids, cocamine compounds, amine oxide, glyceryl monoesters, ethoxylated monocarboxylic and hydroxyl compounds. Additionally, lecithin and Na Cetearyl SO$_4$ have been found to be effective irritation inhibitors.

The preferred amino acids are the water soluble amino acids. The amine oxides of this invention are preferably compounds of the general formula

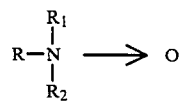

wherein $R_1$ and $R_2$ are independently selected from the group $C_1$–$C_4$ alkyl and R is a $C_{10}$ to $C_{20}$ alkyl, $C_{10}$–$C_{20}$ alkylene cycloalkyl or a heterogeneous cyclic compound containing oxygen, sulfur or nitrogen. Alternately $R_1$, $R_2$ and R may combine to form the cyclic or heterocyclic compound. The glycerol monoesters of this invention are preferably monoesters of $C_{10}$–$C_{30}$ carboxylic acids, and more preferably $C_{15}$–$C_{20}$ carboxylic acids.

The ethyoxylated acid and hydroxyl compounds suitable for use in the practice of this invention have the general formula R—$(X)_n(OCH_2CH_2)_m$OH wherein n is 0 or 1 and X is C=O; when n is 1, m is an integer of about 10 to 100, preferably about 15 to 30 and R is a $C_6$–$C_{30}$ alkyl cycloalkyl or aromatic group. Illustrative examples of R are stearyl, oleyl, phenyl, dodecyl etc.

Cocamine compounds are the primary aliphatic amines derived from coconut oil having the general formula

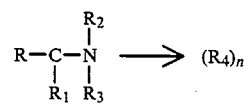

wherein R is the coconut oil radical; n is 0 or 1; $R_1$ is H or O; $R_2$ and $R_3$ are H, alkyl $C_{1-4}$ or $(CH_2)_2OH$; when n=1, $R_4$ is 0 or

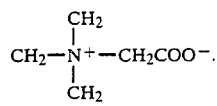

when n is 0, $R_2$ and $R_3$ may form a morpholine ring having the structure

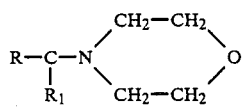

Illustrative non-limiting examples of suitable amino acids are alanine and glycine. Illustrative non-limiting examples of cocamine compounds are cocamide DEA, cocamide MEA and cocamide betaine. Illustrative non-limiting examples of amine oxides are oleamine oxide, lauramine oxide and N-cocomorpholine oxide. Illustrative non-limiting example of glyceryl monoesters suitable for use in the practice of this invention are glycerylmonostearate, glycerylmonostearate (SE) and glycerylhydroxystearate. Other suitable irriation inhibitors include lecithin and sodium cetearyl sulfate.

The irritation inhibitors of this invention are suitable for use with anionic, cationic or nonionic surfactants. They can be used at a weight ratio of irritation inhibitor to surfactant of about 0.25 to 1 to about 40 to 1 preferably about 0.5 to 1 to about 30 to 1 more preferably 1/1 to about 20 to 1. The upper limit of the amount of irritation inhibitor utilized is not critical and is determined primarily by economic considerations. It is only necessary that an effective amount of irritation inhibitor be utilized. An effect amount in terms of weight ratio of inhibitor to surfactant is generally at least 0.25 to 1, preferably at least 0.5 to 1, more preferably at least 1 to 1, most preferably at least 2 to 1.

Each of the irritation inhibitors of this invention were tested against a control which contained only the detergent. The effectiveness of each of the inhibitors was evaluated using in vivo guinea pig immersion tests. The test animals were examined to determine the initial condition of their abdominal skin. The skin was evaluated for erythema, flaking and roughness. Erythema was judged on a visual basis.

Flaking was also evaluated on a visual basis using a Woods' (U.V.A.) light with magnifying glass to enhance perception. The scoring system used is as follows:

| Erythema | Flaking | Roughness |
|---|---|---|
| 0 No effect | 0 No response | 0 Smooth, normal response |
| 1 Slight | 1 Slight response | 1 slight response |
| 2 Moderate | 2 Moderate scaling | 2 Moderate response |
| 3 Severe | 3 Moderate scaling with some sloughing of epidermis | 3 Definite response |
| | | 4 Definite roughness with cracking |
| 4 Severe with hemorrhage | 4 Severe scaling, sloughing of epidermis marked cracking | 5 Severe roughness with deep cracking and oozing. |
| 5 necrosis | 5 Sloughing of large areas of epidermis, deep cracking with possible hemorrhage | |

Transepidermal water loss (TEWL) was evaluated on a daily basis. Skin surface measurements were made in triplicate using the Infrared Thermometer ® (Everest Interscience, Inc.)

TEWL ($g/m^2/hr$) measurements were taken with the Servomed Evaporimeter Ep1 ® (Stockholm). Following the procedures described above each animal's abdominal region was closely clipped of hair with an animal hair clipper (No. 40 head).

In conducting the tests positive control groups (2 animals per group) were immersed for exactly 30 or 60 minutes in surfactant solutions while test animals were immersed in surfactant solution containing irritation inhibitor. The length of immersion was dependent on humidity. At humidity levels above 60% the 60 minute immersion was used since the animal skin was less susceptible to rupture. The immersion procedure was repeated daily for four consecutive days. During the immersion phase the animals were placed in perforated, plastic coated steel canisters with "loc on" lids. These canisters containing the animals were then placed in 2-liter beakers containing approximately 1.2 liters of surfactant solution at 38±2° C. The beakers were then placed in a water bath maintained at 38±2° C.

After the immersion period each animal was removed from the cannister and placed in an open cage which was brought to a surface temperature of approximately 32° C. with an infrared light. After 30 minutes of drying, the animals were returned to their cages. On each of days 2, 3 and 4 each animal was evaluated as discussed above prior to immersion. The animals' skin condition was evaluated on day 5 and the experiment then terminated.

A summary of the results showed a partial protection are effective for some applications such as shampoos or dish washing liquid since the concentration of detergent in the wash solution is low or in contact with the skin for a limited time. However the preferred irritation inhibitors are those which give total protection to the skin especially in such preparations as cleansing creams.

Percents are by weight of the total solution unless otherwise specified.

EXAMPLE 1

Guinea pigs were subjected to in vivo immersion tests using a control solution containing 0.25 wt.% linear alklbenzenesulfonate (LAS) and a test solution containing 0.25 wt.% LAS and 20 wt.% glycerin. The results were plotted on a graph having "Time" (days) as the ordinate and "Response" as the abscissa. The area under the curve was measured for each control and test specimen. The results are shown in Table II. A larger area indicates a greater response or adverse reaction to the solution tested.

It is apparent that at the 20% wt.% level glycerin is an effective anti-irritant. As seen from Table 1 however, at the 2-15 wt.% level glycerine gives only partial protection.

EXAMPLE 2

Example 1 was repeated using sorbitol as the irritation inhibitor over the 3.5–20% range. When used in amounts of between about 3.5 and about 7.5 wt.% based on the solution, sorbitol gave partial protection as an inhibitor when used with LAS. When sorbitol is used in amounts of about 7.5 to about 20 wt.%, total protection is achieved. Areas under the Response vs. Time Curves is shown in Table II for 20 wt.% sorbitol.

EXAMPLE 3

Example 1 was repeated using sucrose as the irritation inhibitor. When sucrose was used in amounts of about 20 wt.% in a solution containing 0.25 wt.% LAS, the sucrose gave total protection.

EXAMPLE 4

Example 1 was repeated using lactose as the irritation inhibitor. In amounts of about 10 wt.% lactose gave complete protection against LAS.

EXAMPLE 5

Example 1 was repeated using urea as the irritation inhibitor. When urea is used in amounts of about 20% by weight in a 0.25 weight % LAS solution, total protection was achieved.

EXAMPLE 6

Example 1 was repeated using N-cocomorpholine oxide as the irritation inhibitor. The N-cocmorpholine oxide gave total protection at about the 0.25% by weight level based in a 0.25 weight % LAS solution.

EXAMPLE 7

Example 1 was repeated using lauramine oxide as the irritation inhibitor. At about 0.25 wt.% lauramine oxide in a 0.25 wt.% solution of LAS, total protection against surfactant insult was achieved.

EXAMPLE 8

Example 1 was repeated using oleamine oxide as the irritation inhibitor. When used in amounts of about 0.25 wt.%, total protection was achieved.

EXAMPLE 9

Example 1 was repeated using hexylene glycol as the irritation inhibitor. At 1% hexylene glycol in a 0.25 wt.% solution of LAS no substantial protection at all was noticable. When the inhibitor was used in amounts of about 2.5 to about 5.0%, total protection was obtained against surfactant irritation.

EXAMPLE 10

Example 1 was repeated using PEG 1000 stearate as the irritation inhibitor. PEG 1000 is an ethoxylated stearic acid. When the inhibitor was used in amounts of about 0.25 wt.% in a 0.25 wt.% solution of LAS, total protection was achieved against surfactant irritation.

EXAMPLE 11

Example 1 was repeated using glycerylmonolaurate as the irritation inhibitor. When amounts of about 0.25 wt.% of inhibitor was used, total protection was achieved against surfactant irritation.

EXAMPLE 12-14

Example 1 was repeated using glycerylmonstearate self-emulsifying (SE), glycerylhydroxystearate and glycerylmonooleate. Each of these compounds gave total protection when used in amounts of about 0.5 wt.% in a 0.25 wt.% LAS solution.

EXAMPLE 15

Example 1 was repeated using as the irritation inhibitors cocamide MEA. When used in amounts of about 0.25 wt.% in the solution there was total protection against surfactant.

EXAMPLE 16

Example 1 was repeated using cocamide DEA as the irritation inhibitor in amounts of about 0.25 wt.% in the surfactant solution. Total protection was achieved against surfactant irritation.

EXAMPLE 17

Example 1 was repeated using cocamide betaine as the irritation inhibitor in amounts of about 0.25 wt.%. in the surfactant solution. Total protection was achieved against surfactant irritation.

EXAMPLE 18-19

Example 1 was repeated using glycine and alanine as the irritation inhibitors. The glycine and alanine were each effective to give total protection against anionic surfactant insult at 7.5 wt.% in a 0.25 wt.% LAS solution.

EXAMPLE 20

Example 1 was repeated using lecithin as the irritation inhibitor. At about the 0.5 wt.% level lecithin gave total protection against surfactant insult.

EXAMPLE 21

Example 1 was repeated using sodium cetearyl sulfate as the irritation inhibitor. Total protection against surfactant irritation was achieved using amounts of about 0.25 wt.% of the inhibitor. This was especially surprising since sodium ceteraryl sulfate is an anionic wetting agent.

It is evident that the preferred irritation inhibitors of this invention are effective at levels which are several orders of magnitude below those required for the prior art polyhydric irritation inhibitors. The irritation inhibitors can be utilized with any linear alkylbenzene sulfonate (LAS). LAS compounds are characterized in that the alkyl group is on a $C_{10}$ or greater alkyl group which is preferably a straight chain moiety but may be iso or branched at its end. Typical of these LAS compounds is sodium dodecylbenzyenesulfonate. The cation of the LAS can be an alkali metal or an ammonium ion. preferably the cation is sodium.

While the irritation inhibitors of this invention are particularly suited for use with anionic surfactants, e.g. LAS, they may advantageously be used in conjunction with cationic and nonionic surfactants. The following examples demonstrate the usefulness of the irritation inhibitor of this invention with certain cationic and nonionic surfactants.

EXAMPLE 22

Protection against surfactant insult from cationic surfactants was evaluated using Lauryl Triammonium chloride as the surfactant. Lauryl Triammonium chloride ("LTC") is a quaternary ammonium salt, specifically dodecyl trimethyl ammonium chloride. Tests are conducted with a 0.5 wt.% solutions of LTC. The irritation inhibitors evaluated were glycerine (20 wt.%), sorbitol 20 (wt.%), glycerylmonostearate (SE) (0.5 wt.%) and oleamide oxide (0.25 wt.%). The qualitative results are shown in Table 1. At the levels tested, the glycerylmonostearate (SE) gave partial protection and the oleamine oxides gave no protection.

EXAMPLE 23

In order to demonstrate the effectivenss of the irritation inhibitors of this invention to prevent surfactant insult with nonionic surfactants a 4 wt.% solution of BRIJ56® (Ceteth 10®, which is the polyethylene glycol ether of cetyl alcohol having 10 polyethylene glycol groups) was used as a control and with various amounts of irritation inhibitors. Oleamine oxide (0.5 wt.%) glycerine (10 wt.%), sodium cetearyl sulfate (1 wt.%) and sodium cetearyl sulfate (1 wt.%) in conjunction with 10 wt.% glycerine all gave partial protection in the guinea pig immersion test. Glycerlymonostearate pig immersion test, irritation inhibitors rated "partial" at a given level give adequate protection for such products as shampoos which are in contact with skin for only a short time. For products such as dishwashing soaps and cleansing cream where there is extended contact with the skin the higher levels which give total protection against surfactant insult are preferred. Those skilled in the art will recognize from the foregoing disclosure that mixtures of the irritation inhibitors of this invention may be utilized as well as the individual inhibitors.

The invention being thus described, it will be obvious by reference to this disclosure that the same may be varied in many ways. Such variations are not to be regarded as a departure from the spirit and scope of the invention and all such modifications are intended to be included within the scope of the claims.

TABLE 1

GUINEA PIG IMMERSION RESULTS

PROTECTION AGAINST ANIONIC SURFACTANT INSULT
(.25% SOLUTION OF LAS, SLS)

| Total Protection | Partial Protection | No Protection |
|---|---|---|
| 20% Glycerine | 2.4–15% Glycerine | 2.0% Mg SO$_4$ |
| 20% Ethanol | 3.5% Sorbitol | 0.1% PVP |
| 7.5–20% Sorbitol | 5% Mannitol | 1% Hexylene Glycol |
| 2.5–5.0% Hexylene Glycol | 20% Propylene Glycol | 0.1 Polyquat H |
| 10% Lactose | 10% Ethanol | 5% Ethanol |
| 20% Urea | 2.5% n-Butanol | 0.1% Polystyrene SO$_3$ |
| 20% Sucrose | 10% n-Propanol | 0.25% Polyox |
| 7.5% Alanine | 0.1% Oleamine Oxide | 10% Corn Syrup |
| 7.5% Glycine | 0.1% Glycerylmonostearate (SE) | |
| 0.5% Lecithin | 0.5% Glycerylisostearate | |
| 0.25% Cocamide DEA | | |
| 0.25% Na Cetearyl SO$_4$ | | |
| 0.25% Oleamine Oxide | | |
| 0.25% Lauramine Oxide | | |
| 0.25% Glycerylmonolaurate | | |
| 0.25% PEG-1000 Stearate | | |
| 0.25% Cocamide Betaine | | |
| 0.5% Glycerylmonostearate (SE) | | |
| 0.5% Glycerylhydroxystearate | | |
| 0.5% Glycerylmonooleate | | |
| 0.25% N—cocomorpholine Oxide | | |
| 0.25% Cocamide MEA | | |

PROTECTION AGAINST CATIONIC SURFACTANTS
(0.5% SOLUTION OF LAURYL TRIMMONIUM ® CHLORIDE)

| Total | Partial | None |
|---|---|---|
| 20% Glycerine | 20% Sorbitol | 0.25% Oleamine Oxide |
| | 0.5% Glycerylmonostearate (SE) | |

PROTECTION AGAINST NONIONIC SURFACTANTS (4% BRIJS)

| Partial | None |
|---|---|
| 0.5% Oleamine Oxide | 0.50% Glyceryl-monostearate (SE) |
| 10% Glycerine | |
| 1% Na Cetearyl SO$_4$ | |
| 1% Na Cetearyl SO$_4$ + 10% Glycerine | |

(SE) gave no protection at the 0.5 wt.% level.

Again it is seen that the irritation inhibitor of this invention are effective at substantially lower concentrations than the prior art polyhydric compounds.

The most significant data point in the guinea pig immersion test evaluation is transepidermal water loss (TEWL). Since this is a direct measure of skin tissue damage, Table II presents these data for the irritation inhibitor of this invention which were tested. The data presented represents the area under the curve Response vs. Time (days) for TEWL. It will be noted that on this basis glycerine utilized at 20 wt.% is not as effective as oleamine oxide at the 0.5 wt.% level.

The level at which the irritation inhibitor is used will depend on the inhibitor, the surfactant and the degree of protection desired. In view of the severity of the guinea

TABLE II

TRANSEPIDERMAL WATER LOSS
AREA UNDER THE RESPONSE TIME CURVES

| Inhibitor (3) | TEWL (2) (g/m$^2$/hr.) | Control (1) |
|---|---|---|
| 20% Glycerine | −33.03 | (4) |
| 20% Ethanol | −35.85 | (4) |
| 7.5–20% Sorbitol | −35.85 | (4) |
| 2.5–5.0% Hexylene Glycol | −49.7 | (4) |
| 10% Lactose | −31.6 | (4) |
| 20% Urea | −32.8 | (4) |
| 20% Sucrose | −28.2 | (4) |
| 7.5% Alanine | −45.75 | (4) |
| 7.5% Glycine | −38.7 | (4) |
| 0.5% Lecithin | −76.3 | (4) |
| 0.25% Cocamide DEA | −62.6 | (4) |

TABLE II-continued

TRANSEPIDERMAL WATER LOSS
AREA UNDER THE RESPONSE TIME CURVES

| Inhibitor (3) | TEWL (2) (g/m²/hr.) | Control (1) |
|---|---|---|
| 0.25% Na Cetearyl SO$_4$ | −47.79 | (4) |
| 0.25% Oleamine Oxide | −36.49 | (4) |
| 0.25% Lauramine Oxide | −67.6 | (4) |
| 0.25% Glycerylmonolaurate | 49.49 | (4) |
| 0.25% PEG-1000 Stearate | 47.4 | (4) |
| 0.25% Cocamide Betaine | −65.2 | (4) |
| 0.50% Glycerylmonostearate (SE)* | −40.06 | (4) |
| 0.5% Glycerylhydroxystearate | 101.5 | (4) |
| 0.5% Glycerylmonooleate | −103.7 | (4) |
| 0.25% N—cocomorpholine Oxide | −100.3 | (4) |
| 0.25% Cocamide MEA | −105.1 | (4) |
| 0.5% Glycerylmonostearate (SE) | −7.43 | (5) |
| 20% Sorbitol | −10.79 | (5) |
| 20% Glycerine | −36.2 | (5) |
| 1% NaCetearyl SO$_4$ | −35.5 | (6) |
| 0.5% Oleamine Oxide | −26.8 | (6) |
| 10% Glycerine | −19.9 | (6) |

*SE stands for self-emulsifying
(1) Control with surfactant only and no irritation inhibitor
(2) (A) TEWL - (B) TEWL = TEWL where (B) is the control and (A) is the test solution comprising the control plus the indicated amount of inhibitor.
(3) wt. % of indicated inhibitor in test solution
(4) 0.25 wt. % LAS/water solution
(5) 0.5 wt. % Lauryl trimethyl ammonium chloride
(6) 4% BRIJ 56 (Ceteth 10 ® which is the polyethylene glycol ether of cetyl alcohol having 10 polyethylene glycol groups).

What is claimed is:

1. A process for preparing a composition for inhibiting surfactant irritation and insult to skin tissue which consists essentially of incorporating sodium cetearyl sulfate as an irritation inhibitor into a water solution of about 0.25 to about 5 wt % of a surfactant, based on the total weight of solution; said surfactant selected from the group consisting of linear alkyl benzene sulfonates, sodium lauryl sulfate, cationic surfactants and nonionic surfactants; and wherein the weight ratio of irritation inhibitor to surfactant is at least 0.25 to 1.

2. The process according to claim 1 wherein the surfactant is a linear alkyl benzene sulfonate.

3. The process according to claim 2 wherein the linear alkylbenzene sulfonate is dodecylbenzene sulfonate.

4. The process according to claim 3 wherein the dodecylbenzene sulfonate is sodium dodecylbenzene sulfonate.

5. The process according to claim 1 wherein the weight ratio of inhibitor to surfactant is at least 0.5 to 1.

6. The process according to claim 1 wherein the weight ratio of inhibitor to surfactant is at least 1 to 1.

7. The process according to claim 1 wherein the weight ratio of inhibitor to surfactant is at least 2 to 1.

8. The process according to claim 1 wherein the surfactant is a nonionic surfactant.

9. The process according to claim 8 wherein the surfactant is the polyethylene glycol ether of cetyl alcohol having 10 polyethylene glycol groups.

10. A cleansing composition capable of efficient cleaning without irritation to skin consisting essentially of a water solution of about 0.25 to about 5 wt. % of a surfactant, based on the total weight of solution, and sodium cetearyl sulfate as an irritation inhibitor; said surfactant selected from the group consisting of linear alkyl benzene sulfonates, sodium lauryl sulfate, cationic surfactants and nonionic surfactants; and wherein the weight ratio of irritation inhibitor to surfactant is at least 0.25 to 1.

11. The composition according to claim 10 wherein the weight ratio is at least 0.5 to 1.

12. The composition according to claim 11 wherein the weight ratio is at least 1 to 1.

13. The composition according to claim 11 wherein the weight ratio is at least 2 to 1.

14. The composition according to claim 10 wherein the surfactant is a linear alkyl benzene sulfonate.

15. The composition according to claim 14 wherein the linear alkylbenzene sulfonate is dodecylbenzene-sulfonate.

16. The composition according to claim 15 wherein the dodecylbenzene sulfonate is sodium dodecylbenzene sulfonate.

17. The composition according to claim 10 wherein the surfactant is a cationic surfactant.

18. The composition according to claim 17 wherein the surfactant is dodecyltrimethyl ammonium chloride.

19. The composition according to claim 10 wherein the surfactant is a nonionic surfactant.

20. The composition according to claim 19 wherein the surfactant is the polyethylene glycol ether of cetyl alcohol having 10 polyethylene glycol groups.

21. The composition according to claim 10 wherein the weight ratio of irritation inhibitor to surfactant is about 0.25 to 1 to about 40 to 1.

* * * * *